(12) United States Patent
Stich et al.

(10) Patent No.: US 9,372,170 B2
(45) Date of Patent: Jun. 21, 2016

(54) GAS SENSOR

(71) Applicant: Testo AG, Lenzkirch (DE)

(72) Inventors: Ralf Stich, Buchenbach (DE); Peter Ziegler, Riegel (DE); Luciana Pitta-Bauermann, Freiburg (DE)

(73) Assignee: Testo AG, Lenzkirch (DE)

( * ) Notice: Subject to any disclaimer, the term of this patent is extended or adjusted under 35 U.S.C. 154(b) by 326 days.

(21) Appl. No.: 13/975,655

(22) Filed: Aug. 26, 2013

(65) Prior Publication Data

US 2014/0061047 A1 Mar. 6, 2014

(30) Foreign Application Priority Data

Aug. 24, 2012 (DE) .................... 10 2012 016 816

(51) Int. Cl.
*G01N 27/407* (2006.01)
*G01N 27/403* (2006.01)

(52) U.S. Cl.
CPC ........ *G01N 27/4071* (2013.01); *G01N 27/4035* (2013.01)

(58) Field of Classification Search
None
See application file for complete search history.

(56) References Cited

U.S. PATENT DOCUMENTS

| 5,338,429 | A | * | 8/1994 | Jolson | ............... G01N 27/4045 204/412 |
| 7,981,266 | B2 | * | 7/2011 | Mett | ..................... B82Y 15/00 204/400 |
| 2009/0095626 | A1 | * | 4/2009 | Dutta | ................. G01N 27/4075 204/424 |
| 2010/0301871 | A1 | | 12/2010 | Biskupski | |
| 2012/0211362 | A1 | | 8/2012 | Onkawa et al. | |

FOREIGN PATENT DOCUMENTS

| DE | 102007059653 | | 6/2009 |
| DE | 102012202716 | | 8/2012 |
| EP | 0299779 | * | 1/1989 |
| WO | 0114864 | | 3/2001 |
| WO | 2012071151 | | 5/2012 |

* cited by examiner

*Primary Examiner* — Jennifer Dieterle
(74) *Attorney, Agent, or Firm* — Volpe and Koenig, P.C.

(57) ABSTRACT

In an electrochemical gas sensor (1), a carrier substrate (2) has an underside (3) and a top side (4), wherein an electrode structure (20) with an electrolyte layer (6) is arranged at the top side (4), while a gas inlet for a measurement gas is formed at the underside (3). A porous region (7) formed of a porous material is provided in the carrier substrate (2), such that diffusion openings in the porous material connect the underside (3) to the top side (4) in a gas-permeable manner, and a connection (5, 27) of a measurement electrode (25, 26) is formed in a gas-tight surface region (33, 34, 35) at the top side (4) adjacent to the porous region (7) and the connection (5, 27) is at least partly covered by the electrolyte layer (6).

19 Claims, 5 Drawing Sheets

GAS SENSOR

BACKGROUND

The invention relates to a gas sensor comprising a carrier substrate having a top side and an underside, wherein a gas inlet for a measurement gas is formed at the underside and wherein an electrode structure with an electrolyte layer is arranged on the top side, wherein the carrier substrate has a porous region comprised of a porous material and the porous material forms diffusion openings that connect the underside to the top side.

WO 2012/071151 A1 discloses such a gas sensor, wherein the electrode structure is applied directly to a porous carrier substrate and wherein the porous carrier substrate, on its underside facing away from the electrode structure, is provided with a back plate in order to delimit the gas entrance into the carrier substrate to an access opening.

Gas sensors are also known in which, for the purpose of conducting gas through the carrier substrate from the underside to the top side, drilled holes are introduced into the carrier substrate.

It has been found that such drilled holes have the disadvantage that the electrolyte applied or a catalyst coating arranged between electrolyte and electrode structure can penetrate into the drilled holes and close them during the coating process or later. This can have the consequence that the measurement gas can no longer reach the electrode structure at the top side of the carrier substrate during operation, as a result of which a proper function of the gas sensor is no longer ensured.

It has furthermore been found that applying the electrode structure on a porous carrier substrate is technologically complex.

SUMMARY

The invention addresses the objective of providing a gas sensor which can be produced in a simple manner.

In order to meet this objective, in the case of a gas sensor of the type described in the introduction, according to the invention it is provided that a gas-tight surface region is formed at the carrier substrate at the top side adjacent to the porous region, that a connection of a measurement electrode of the electrode structure is formed as a metallic coating on the gas-tight surface region and that the electrolyte layer at least partly covers the connection and the region. What is advantageous in this case is that the at least one connection adheres well on the gas-tight surface region. This simplifies the production of the gas sensor. What is furthermore advantageous in this case is that the diffusion openings of the porous material are so small that an exterior coating of the carrier substrate does not pass into the diffusion openings, or passes into them only insignificantly, during application due to the surface tension of the coating and the wetting properties. Precautions for preventing the electrolyte layer from penetrating into the diffusion openings during production or during operation, which precautions are complex in terms of production engineering, can thus be dispensed with. Preferably, the catalyst layer completely covers the porous region and/or the connection.

The gas-tight surface region can be formed, for example, by virtue of the carrier substrate being formed of a gas-tight material into which porous regions are introduced, in particular by equipping and/or filling one or a plurality of openings extending continuously between underside and top side of the carrier substrate with a porous material, or in which the porous regions are formed, for example by subsequent material alteration.

In one configuration of the invention it can be provided that the electrode structure has at least two measurement electrodes. In this case, one measurement electrode of the at least two measurement electrodes can be embodied as a working electrode and a further measurement electrode of the at least two measurement electrodes can be embodied as a counterelectrode. Preferably, the electrode structure additionally has a reference electrode. The reference electrode can differ from the other measurement electrodes in that it is terminated in a gas-tight manner relative to the gas inlet.

In one configuration of the invention it can be provided that the porous material is embodied in a hydrophobic fashion. This is particularly expedient if the electrolyte is water-based. What is advantageous in this case is that the porous material forms an additional protection against leakage of the electrolyte, that is to say escape of the electrolyte from the gas sensor.

In one configuration of the invention it can be provided that the measurement electrodes and/or the reference electrode in each case have/has a connection embodied as a coating of the carrier substrate. The coating is preferably comprised of gold. The voltage between working electrode and reference electrode is kept constant by the connections. A current is generated between the working electrode and the counterelectrode during the oxidation or reduction of the measurement gas, said current being measured. Preferably, the connections of the electrode structure are embodied as metallic coating, for example comprised of gold. It is particularly expedient if the connections are printed onto the carrier substrate. What is advantageous in this case is that simple production is possible.

In one configuration of the invention it can be provided that the measurement electrodes and/or the reference electrode in each case have/has a catalyst layer arranged between the or a respective connection and the electrolyte layer. The catalyst layer thus forms the measurement electrodes and/or the reference electrode. What is advantageous in this case is that it is possible to realize measurement methods in which the measurement gas that diffuses into the gas sensor through the diffusion openings is fed to a catalyst in which the desired electrochemical reaction proceeds.

By way of example, the catalyst layer can be formed of platinum or contain platinum. Carbon, for example in the form of carbon nanotubes (CNT), can also be used as catalyst.

In this case, it can be provided that the catalyst layers of the measurement electrodes, that is to say of the working electrode and of the counterelectrode, and of the reference electrode are formed of the same material and/or have the same composition. However, it can also be provided that different materials are used as catalyst layer for the working electrode and the counterelectrode or for the working electrode and the reference electrode. By way of example, the catalyst layer of the working electrode can contain platinum, while the catalyst layer of the counterelectrode contains carbon nanotubes. Other material combinations can also be used and are coordinated with the measurement gas to be detected in each case.

It can be provided that the connections form through-openings for the measurement gas. What is advantageous in this case is that the diffusion openings can open in the region of the through-openings, such that the measurement gas can be fed through the through-openings directly to the measurement electrodes of the electrode structure. Particularly compact gas sensors can thus be formed.

In this case, it can be provided that the through-openings have a larger diameter, in particular a diameter at least 50 times or even 100 times larger, than the diffusion openings. What is advantageous in this case is that the position of the through-openings does not have to be exactly aligned with the position of the diffusion openings. Rather, it can be provided that the diameter of the through-openings is chosen to be sufficiently large and the position of the diffusion openings is chosen to be sufficiently close relative to one another that in any case at least one diffusion opening opens at the through-opening.

By way of example, the diffusion openings can have a pore diameter of 50 μm or less, while the through-openings are embodied in a macroscopic fashion and have a clear width of at least 3 mm.

It is particularly expedient if the or each connection surrounds the or a porous region in a ring-shaped fashion. What is advantageous in this case is that contact can be made with the electrodes well on all sides on the top side.

In one configuration of the invention it can be provided that the or a reference electrode is arranged completely on a gas-tight surface region. What is advantageous in this case is that contact between the reference electrode and the measurement gas can be prevented.

Generally, it can be provided that the gas-tight surface region is formed by a barrier layer. Preferably, the barrier layer is produced from a gas-tight plastic, for example from non-expanded or gas-tight PTFE. What is advantageous in this case is that a carrier substrate comprised of a uniform material, for example comprised of a porous material, can be used. The barrier layer is thus printable. What is furthermore advantageous is that a great diversity of shapings of the electrode structure can be produced in a simple manner. The barrier layer thus acts as an intermediate layer between a porous material and the connections.

Alternatively, it can be provided that the gas-tight surface region is formed as the top side of a gas-tight material of the carrier substrate. By way of example, this can be achieved in the case of a bipartite embodiment of the carrier substrate, in which an opening extending continuously from the top side to the underside is filled or equipped with a porous material, by virtue of the surface region being arranged adjacent to the continuous opening. Preferably, the gas-tight material is produced from a gas-tight plastic, for example from gas-tight or non-expanded PTFE, or ceramic.

In one configuration of the invention it can be provided that at least some of the diffusion openings have branches. What is advantageous in this case is that blockages of diffusion openings in certain regions do not immediately lead to the failure of the gas sensor, since the branches provide alternative diffusion paths for the measurement gas.

In one configuration of the invention it can be provided that the diffusion openings are formed with an irregular arrangement in the porous region. What is advantageous in this case is that, independently of the specifically chosen form of the electrode structure, it can generally be ensured that diffusion openings are provided at the top side of the carrier substrate in regions left free by the electrode structure, for example through-openings of the electrode structure.

It can also be provided that at least some of the diffusion openings have at least one bend or at least one curve. It is thus possible to form additional barriers which prevent the electrolyte layer and/or the catalyst layer from escaping from the gas sensor through the diffusion openings.

It can also be provided that the diffusion openings form a net-shaped arrangement. By way of example, the diffusion openings can be formed by interspaces between grains welded to one another or connected to one another in some other way. This can be produced in a particularly simple manner.

In order to simplify production, it can be provided that the diffusion openings are formed naturally. By way of example, this can be achieved by sintering or using fillers, preferably volatile fillers, or an expended plastic, for example expanded PTFE (ePTFE), or some other gas-permeable expanded plastic. What is advantageous in this case is that additional production steps, such as drilling or the like, by means of which the diffusion openings are introduced subsequently can be avoided. As a result, it is possible to form branches in the diffusion openings in a particularly simple manner. The size and quantity of the diffusion openings controls the volume of the measurement gas which is detected by the gas sensor.

Alternatively or additionally it can be provided that the diffusion openings are formed by an etching process.

In one configuration of the invention it can be provided that the porous region comprised of porous material is formed by filling or equipping a continuous opening in the preferably gas-tight carrier substrate with a porous material. In this case, the continuous opening connects the underside to the top side. Multipartite carrier substrates can thus be formed. In this case, the continuous opening can connect the top side of the carrier substrate to the underside of the carrier substrate and have a rectilinear course, for example. What is advantageous in this case is that the continuous opening can be produced in a simple manner, for example by drilling, milling, stamping or using casting technology. It is possible to form continuous openings which are comparatively large in terms of diameter, in particular large in comparison with a diameter of the diffusion openings. This can be handled more easily in terms of production engineering. The process of filling or equipping can likewise be carried out in a simple manner, such that overall particularly simple producibility of the porous region comprised of a porous material can be achieved. The filling or equipping can also be formed by inserting, in particular press-fitting, a porous shaped part. It is advantageous if the porous shaped part is formed of a hydrophobic or even very hydrophobic material. This significantly improves protection as a result of leakage of the electrolyte.

Preferably, the carrier substrate is produced integrally from porous material, such that the porous region comprised of the porous material forms the carrier substrate, or the carrier substrate is comprised of at least two constituents in a multi-partite fashion. Said constituents can be connected to one another cohesively or in a positive locking manner or in a force-locking manner. It is particularly expedient if the carrier substrate is comprised of a gas-tight constituent and a porous constituent.

For many applications it is expedient if the carrier substrate is embodied in a planar fashion. In this case, a planar embodiment is understood to mean a configuration in which one dimension, the thickness, is significantly smaller than two dimensions that are complementary to said dimension for forming a three-dimensional object. The carrier substrate is therefore approximately two-dimensional or areal. What is advantageous in this case is that it is possible to achieve compact arrangements which can be used universally or at least diversely.

It can be provided that the carrier substrate is embodied in a tubular fashion. What is advantageous in this case is that the carrier substrate can also perform additional technical functions.

By way of example, it can be provided that the carrier substrate is embodied as part of the measurement gas line.

It can be provided that the carrier substrate is produced from a flexible material. By way of example, the carrier substrate can be produced from film or as a membrane. What is advantageous in this case is that the carrier substrate with the applied coating can be applied to differently configured surfaces. What is furthermore advantageous is that films or membranes form carrier substrates which naturally have diffusion openings or which can be equipped with diffusion openings in a simple manner as early as during production.

In one configuration of the invention it can be provided that on the top side of the carrier substrate in surface regions adjacent to the measurement electrodes, a barrier layer is applied for closing the diffusion openings in these surface regions. This makes it possible to prevent the measurement gas from being able to enter through the diffusion openings in these adjacent regions directly to the reference electrode or into the electrolyte layer.

It can be provided that the electrolyte layer is embodied in a continuous fashion and covers the measurement electrodes and preferably the or a reference electrode. What is advantageous in this case is that the electrolyte layer can be applied in one work operation. What is furthermore advantageous is that diffusion of the measurement gas between the measurement electrodes, that is to say, for example, from the working electrode to the counterelectrode, through the electrolyte layer is made possible. Consequently, it is also possible to form gas sensors which do not have a porous region at the counterelectrode. By way of example, such a gas sensor can be designed for CO measurement.

In one configuration it can be provided that the connections of the measurement electrodes and/or of the reference electrode are embodied as a gold coating. It has been found that the gold coating can readily be applied to the gas-tight surface region. The combination of a gold coating on a surface comprised of non-expanded PTFE has particularly good processing properties.

In one configuration of the invention it can be provided that the connections are applied by coating, in particular by a printing, spraying and/or dispersing method, that is to say are printed, for example. Alternatively or additionally it can be provided that the catalyst layer is printed. It can also be provided that the electrolyte layer is applied by coating, in particular by a printing, spraying and/or dispersing method, that is to say is printed, for example. Preferably, at least two or even all three coatings are printed. It can be provided, for example, that the electrode structure with the connections and the catalyst layer and, if appropriate, the reference electrode of the electrode structure is/are applied to the carrier substrate by coating, in particular by a printing, spraying and/or dispersing method, that is to say is/are printed, for example.

In order to prevent the electrolyte layer from flowing out through the diffusion openings, it can additionally be provided that the electrolyte layer is in gel form or solid. This can be achieved, for example, by the electrolyte layer being in gel form or even solid as a result of addition of particulate or particle-type constituents. In this case, a gel is understood to mean a dimensionally stable, readily deformable disperse system rich in liquids and/or gases and comprising at least two components, wherein the components include the particulate constituents as thickener, on the one hand, and a liquid, for example an ionically conductive medium such as an acid or alkaline solution, as dispersant, on the other hand. What is advantageous in this case is that the gel-type or even solid consistency of the electrolyte layer prevents, or prevents to the greatest possible extent, the electrolyte layer from being able to escape through the diffusion openings or in some other way. Consequently, the durability or temporal stability of the gas sensor can again be increased. In this case, the particulate or particle-type constituents can be added to a liquid, preferably highly ionically conductive, medium in order to obtain the desired consistency.

In one configuration of the invention it can be provided that the catalyst layer covers the connections of the measurement electrodes and/or of the reference electrode. What is advantageous in this case is that a compact design can be achieved.

It can also be provided that the electrolyte layer covers the entire top side of the carrier substrate. What is advantageous in this case is that the electrolyte layer can be applied areally in a particularly simple manner. For this purpose, it is preferably possible to provide a barrier layer for closing the diffusion openings which open in regions adjacent to the electrode structure.

In one configuration of the invention it can be provided that the electrolyte layer covers the electrode structure. What can thus be achieved, in particular, is that the electrolyte layer covers the measurement electrodes and/or the reference electrode. What can thus also be achieved is that the electrolyte layer covers the catalyst layer. Large-area electrolyte layers can thus be used.

In order to prevent the electrolyte layer from drying out or evaporating or aging in some other way over the course of time, it can be provided that a cover layer is applied on the or on the outer side around the electrolyte layer. The cover layer is preferably cured. A temporal constancy of the form and/or composition of the electrolyte layer can thus be ensured.

It can also be provided that a preferably trough-shaped housing part is arranged on the or on the outer side around the electrolyte layer. What is advantageous in this case is that the electrolyte layer can be protected in a simple manner against alterations and against mechanical actions from outside.

In one configuration of the invention it can be provided that at least two carrier substrates are arranged in a manner spaced apart from one another in a sandwich design, an electrode structure in each case being formed at said carrier substrates. In this case, it is preferably provided that the electrolyte layer is arranged between the two carrier substrates. The two carrier substrates can each have a porous region comprised of a porous material, wherein each porous region is connected to the gas inlet. In this case, each carrier substrate of the two carrier substrates with the associated electrode structure and the electrolyte layer forms per se a gas sensor according to the invention.

Alternatively, it can be provided that only one of the two carrier substrates has a region comprised of a porous material which is connected to the gas inlet. In this case, a measurement electrode of the electrode structure not connected to the gas inlet can be used as a reference electrode, for example. It can thus be provided that a reference electrode is formed at a surface of the electrolyte which faces away from the gas inlet.

BRIEF DESCRIPTION OF THE DRAWINGS

The invention will now be described in greater detail on the basis of exemplary embodiments, but is not restricted to these exemplary embodiments. Further exemplary embodiments arise through combination of individual or a plurality of features of the claims among one another and/or with individual or a plurality of features of the exemplary embodiments.

In the figures.

DETAILED DESCRIPTION OF THE PREFERRED EMBODIMENTS

Figure 1:
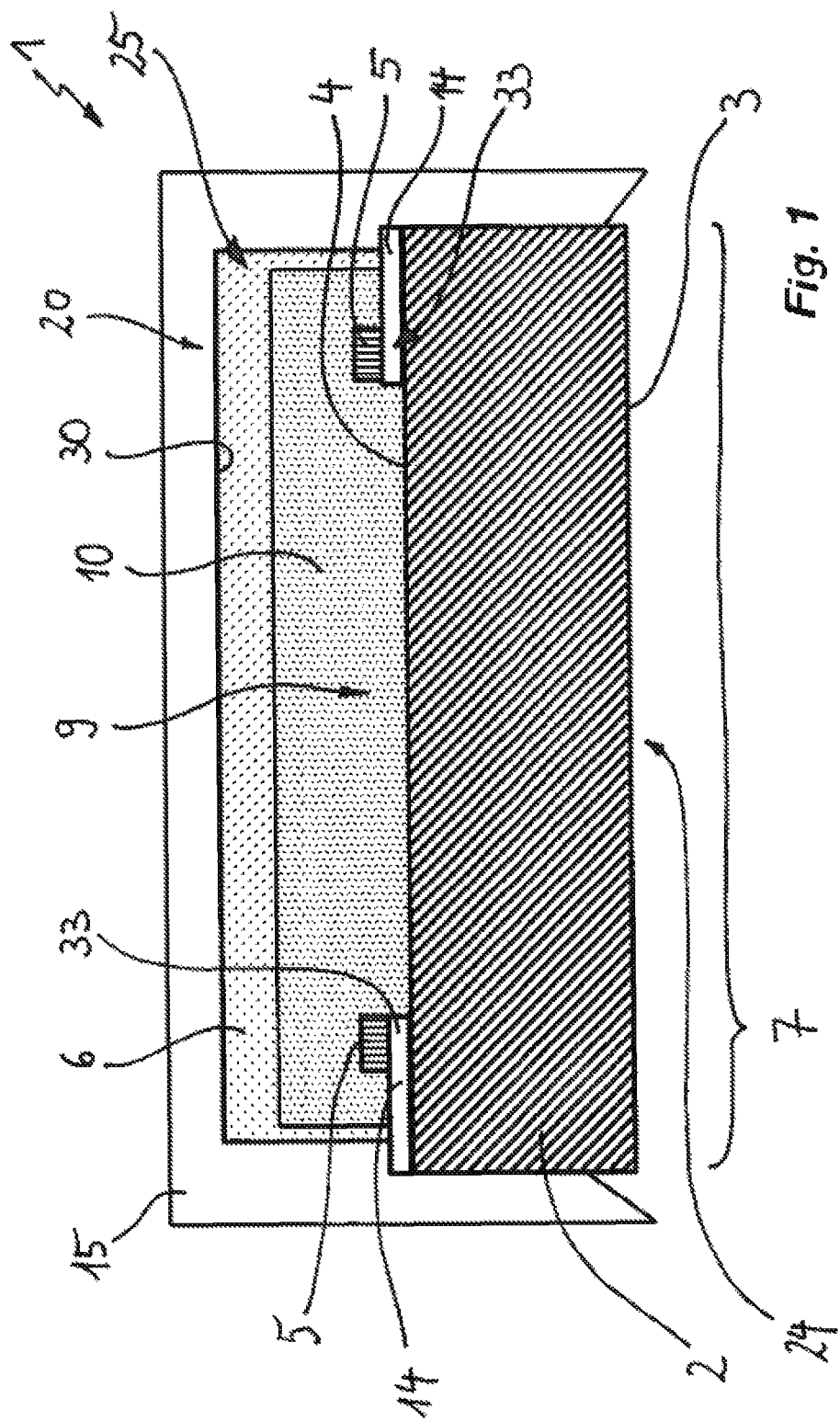
FIG. 1 shows a greatly simplified sectional illustration of a gas sensor according to the invention.

FIG. 1 shows highly schematically in a sectional illustration an electrochemical gas sensor, designated in its entirety by 1.

The gas sensor 1 has a planar carrier substrate 2. In the sectional illustration in FIG. 1, the sectional plane is perpendicular to the plane predefined by the planar carrier substrate 2. The carrier substrate 2 is thus embodied in an areally planar fashion.

The carrier substrate 2 has an underside 3. A gas inlet 24—which is not illustrated further and is known per se—for a measurement gas is formed at the underside 3. Via this gas inlet 24, the measurement gas can be fed to the underside 3 of the carrier substrate 2.

An electrode structure 20 is formed at the top side 4 of the carrier substrate 2, that is to say at the opposite side of the carrier substrate 2 in relation to the underside 3. The electrode structure 20 is designed for detecting and/or generating electrical measurement signals of the gas sensor 1 in a manner known per se. For this purpose, the electrode structure 20 has at least two measurement electrodes 25, 26, for example a working electrode 25 and a counterelectrode 26, and if appropriate a reference electrode. FIG. 1 illustrates only the working electrode 25—the counterelectrode 26 with a connection 27 can be embodied—if appropriate with different choice of material—identically or similarly to the working electrode 25.

Connections 5, 27 of the measurement electrodes 25, 26 of the electrode structure 20 are printed from a metallic material, for example at least partly from gold.

Furthermore, an electrolyte layer 6 is applied and arranged on the top side 4.

The carrier substrate 2 is embodied in an integral fashion. The carrier substrate 2 is produced from a porous material, for example expanded polytetrafluoroethylene (PTFE), and has a porous region 7 comprised of a porous material.

The porous material in the region 7 forms an irregular arrangement of diffusion openings, which are merely indicated by hatching in FIG. 1. The number of diffusion openings is actually very large and corresponds to the natural number of diffusion openings in a porous material.

The diffusion openings connect the underside 3 to the top side 4, such that the measurement gas flowing in via the underside 3 can diffuse to the top side 4.

The connections 5, 27 of the electrode structure 20 has through-openings 9.

Some of the diffusion openings open at the through-opening 9. Consequently, the measurement gas can emerge from the diffusion openings through the through-openings 9 into the measurement electrodes 25, 26.

The clear diameters of the through-openings 9 are greater than the clear diameters of the diffusion openings, such that independently of the precise positioning of the electrode structure 20 on the carrier substrate 2 with the irregular arrangement of the diffusion openings it is ensured that always at least one diffusion opening opens in the through-openings 9.

The diffusion openings are formed by sintering or using volatile fillers, expanded plastic or by an etching process and have branches and/or bends and/or curves.

The diffusion openings thus form an irregular or random net or network of connections or channels between the underside 3 and the top side 4.

In further exemplary embodiments, the diffusion openings can also be formed by microscopic interspaces between grains which are connected, in particular welded, to one another. An irregular net of diffusion openings can thus be formed. From among the latter, individual diffusion openings do not run completely between the underside 3 and the top side 4, but rather end in the carrier substrate 2 as a blind end. By way of example, polystyrene can be used in this case in order to form the porous region.

A catalyst layer 10 is in each case arranged on the connections 5, 27 of the electrode structure 20 and the electrolyte layer 6 in FIG. 1, said catalyst layer forming the measurement electrodes 25, 26 and a reference electrode (not illustrated any further). In this case, the catalyst layers 10 of the measurement electrodes 25, 26 are arranged in a manner spaced apart from one another and are therefore not electrically connected to one another. The measurement gas therefore passes from the diffusion openings through the through-openings 9 into the catalyst layer 10 of the measurement electrodes 25, 26.

The catalyst layer 10 contains platinum, for example, as catalytic material and possibly additional constituents. The catalyst layer 10 can be printed onto the connections 5, 27.

The measurement gas that has passed through the through-openings 9 is then oxidized or reduced at the measurement electrodes 25, 26 of the electrode structure 20, and a current between the connections 5 and 27 of the electrode structure 20 is provided as an electrical measurement signal of the gas sensor 1 and is detected by evaluation electronics (not illustrated any further).

A barrier layer 14 is applied between the parts of the electrode structure 20 and in regions of the top side 4 which are adjacent to the electrode structure 20, said barrier layer closing the diffusion openings in this region. Consequently, no measurement gas can emerge in surface regions which are adjacent to the electrode structure 20. No barrier layer 14 is applied to the through-openings 9. A barrier layer 14 is formed between the carrier substrate 2 and a reference electrode (not shown any further), said barrier layer preventing the measurement gas from penetrating into the reference electrode.

The barrier layer 14 simultaneously serves as an adhesion promoter for the connection 5 and likewise for the connections 27, 28 (not illustrated any further). The barrier layer 14 therefore forms a gas-tight surface region 33 adjacent to the porous region 7, in which surface region the connection 5 and the connections 27 and if appropriate 28 (not illustrated any further) are printed.

The barrier layer 14 is produced from non-expanded PTFE. The connections 5, 27, 28 comprised of gold are applied to the barrier layer.

The connection 5- and likewise the connection 27—is embodied in a ring-shaped fashion and thus encloses the through-opening 9 on all sides.

In further exemplary embodiments, C- or U-shaped connections 5, 27 are formed, and the connections 5, 27 delimit the through-opening 9 only at three sides. In further exemplary embodiments, other shapings of the connections 5, 27 are realized which produce sufficient contact with the catalyst layer 10 of the measurement electrodes 25, 26 and keep free enough area for the passage of the measurement gas to the catalyst layer 10.

It can be seen from FIG. 1 that the electrolyte layer 6 covers the measurement electrodes 25, 26 that is to say in particular the catalyst layers 10 thereof, and the barrier layer 14.

A trough-shaped housing part 15 is placed onto the electrolyte layer 6 on the outer side, which housing part delimits and closes off the electrolyte layer 6 toward the outside. The trough-shaped housing part 15 is latched with the carrier substrate 2 and has the effect of forming a housing for the gas sensor 1. The housing part 15 forms a recess 30 on the inner side, said recess accommodating the electrolyte layer 6 with the electrode structure 20.

Figure 2:
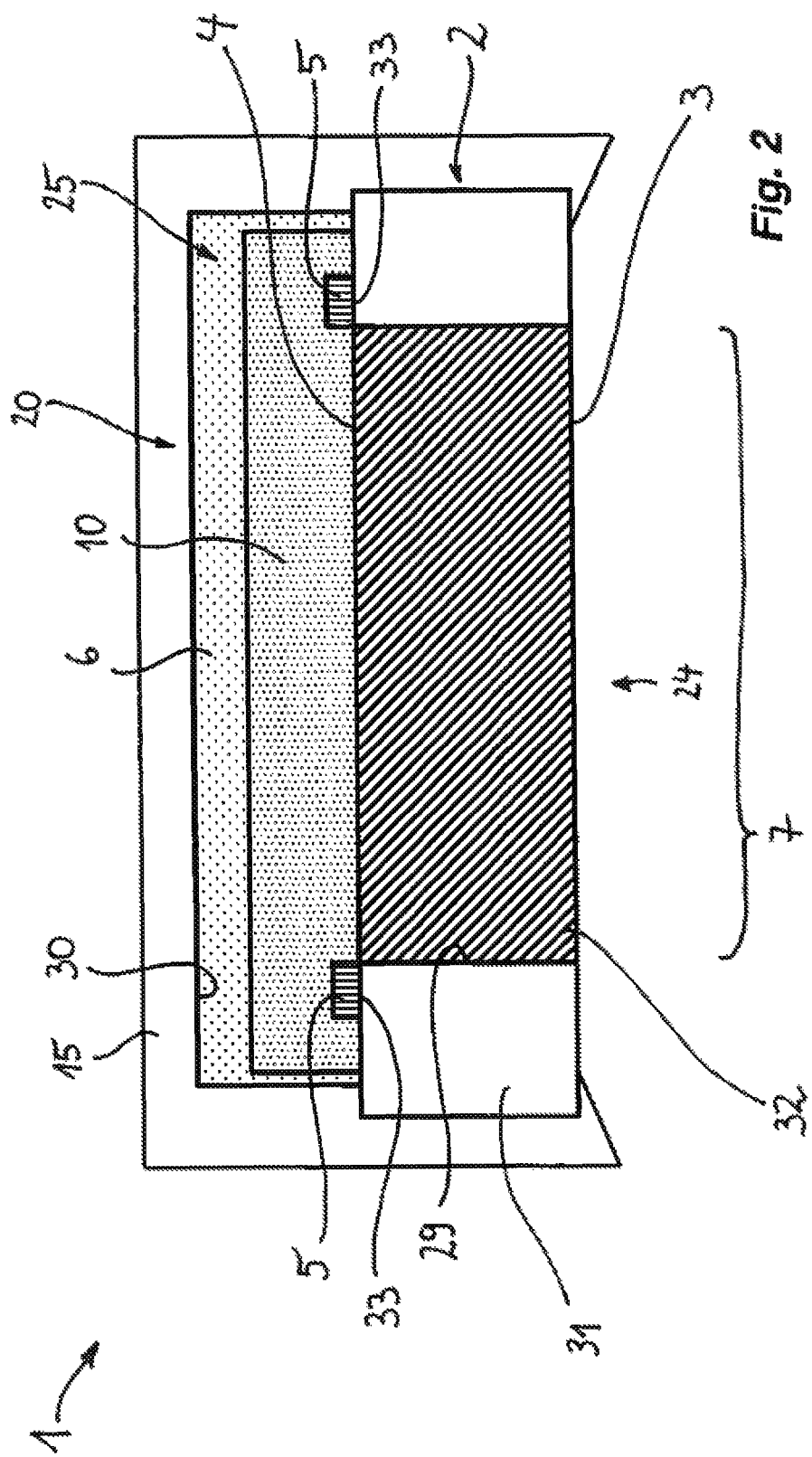
FIG. 2 shows a greatly simplified sectional illustration of a further gas sensor according to the invention with a multipartite carrier substrate.
Figure 3:
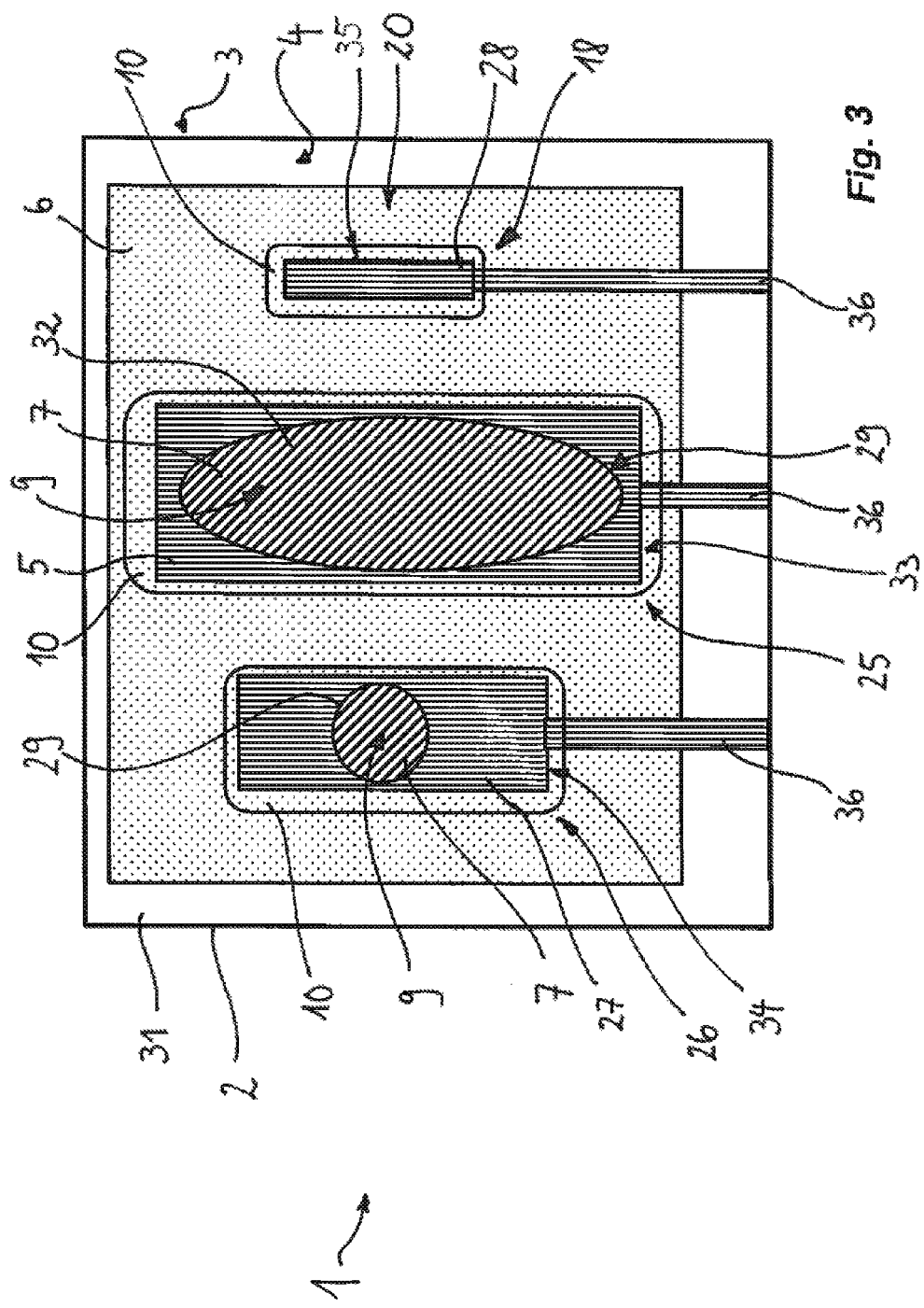
FIG. 3 shows a plan view of the gas sensor in accordance with FIG. 2.

FIG. 2 and FIG. 3 show a further exemplary embodiment of the invention.

Components that are functionally and/or structurally similar to the exemplary embodiment according to FIG. 1 or of the same type are designated by the same reference signs and will not be described separately again. Rather, the explanations concerning FIG. 1 are correspondingly also applicable to the exemplary embodiment according to FIG. 2 and FIG. 3.

FIG. 2 does not show the counterelectrode 26 and the reference electrode 18, in order to simplify the illustration.

In contrast to the exemplary embodiment according to FIG. 1, in which the carrier substrate 2 is embodied integrally, the carrier substrate 2 in the exemplary embodiment according to FIG. 2 and FIG. 3 is embodied in a multipartite fashion. A continuous opening 29 is stamped or cut out or drilled or introduced in some other way into a first constituent 31 of the carrier substrate 2, said first constituent being produced from a gas-tight material.

An appropriately embodied second constituent 32 of the carrier substrate 2 is inserted into the continuous opening 29. The second constituent 32 is connected to the first constituent 31 cohesively and/or in a gas-tight manner.

The second constituent 32 is produced from a porous material as a shaped body and forms the porous region 7 comprised of porous material. The porous region 7 thus is formed of a plurality of non-continuous regions.

The first constituent 31, at its electrode-side surface, provides gas-tight surface regions 33, 34, 35, on which the connections 5, 27, 28 are formed.

In addition, a barrier layer 14 can be applied to the first constituent 31. However, said barrier layer is not absolutely necessary since the first constituent 31 is already embodied in a gas-tight fashion.

It can be seen from FIG. 3 that the porous regions 7 comprised of porous material are enclosed at their edges by a connection 5 and 27 of the measurement electrodes 25, 26 in a ring-shaped fashion. Consequently, the through-openings 9, already discussed with regard to FIG. 1, are almost as large as the regions covered by the measurement electrodes 25, 26.

Furthermore, a reference electrode 18 is formed on the first constituent 31. Although the first constituent 31 is already formed from gas-tight material, a barrier layer 14 can additionally be applied in the region of the reference electrode 18 in order to rule out the emergence of gas into the reference electrode 18.

In further exemplary embodiments, the counterelectrode 26 can be formed completely on the gas-tight surface region 34. Consequently, no porous region 7 is formed in the region of the counterelectrode 26. The measurement gas can enter into the electrolyte layer 6 for example through the porous region 7 of the working electrode and can diffuse through said electrolyte layer to the counterelectrode 26.

Figure 4:
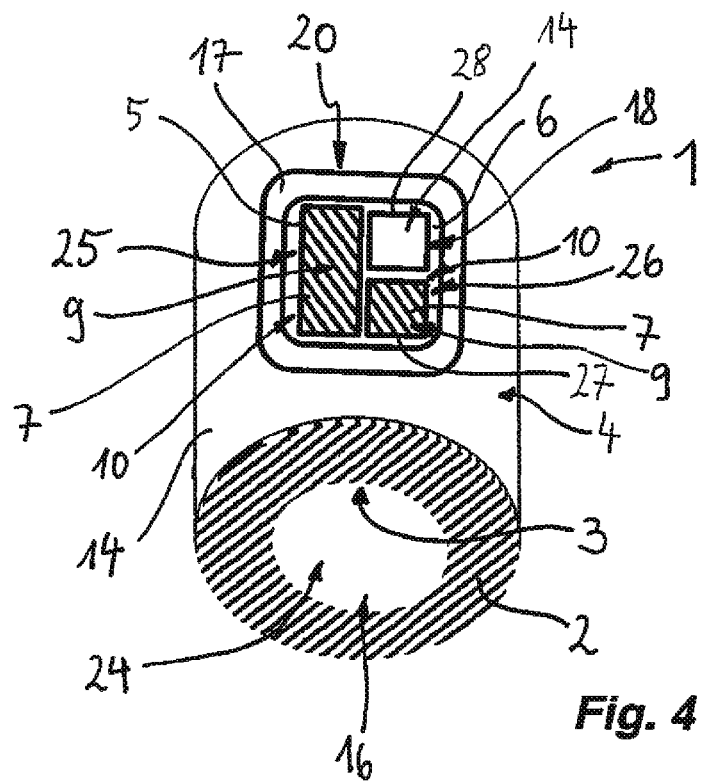
FIG. 4 shows a gas sensor according to the invention with a tubular carrier substrate in a greatly simplified, three-dimensional perspective view.

FIG. 4 shows an exemplary embodiment of a gas sensor 1 according to the invention in which the carrier substrate 2 is not embodied in a planar fashion, but rather in a tubular fashion.

In the exemplary embodiment in accordance with FIG. 4, components that are functionally and/or structurally of the same type as the exemplary embodiment according to FIG. 1 are designated by the same reference signs and will not be described separately again.

In FIG. 4, the underside 3 of the gas sensor 1 is formed at the inner side of the tubular carrier substrate 2, while the top side 4 is formed by the outer side of the tubular carrier substrate 2.

The tubular carrier substrate 2 is thus formed as part of a measurement gas line 16 to which the gas sensor 1 is connected via the diffusion openings (not illustrated any further) in the porous regions 7 in the carrier substrate 2.

Consequently, the measurement gas transported in the measurement gas line 16 can diffuse directly through the diffusion openings from the underside 3 to the measurement electrodes 25, 26 of the electrode structure 20 at the top side 4 of the carrier substrate 2.

By contrast, the reference electrode 18 is sealed against entry of the measurement gas by a barrier layer 14.

In order to form the measurement electrodes 25, 26 the connections 5, 27 are covered with a catalyst layer 10 which supports or enables the reaction at the measurement electrodes 25, 26 of the electrode structure 20. The reaction brings about an electrochemical reaction with ion transport in the electrolyte layer 6 which generates a measurable current at the electrode structure 20 between the connections 5, 27.

Between the connections 5, 27, on the one hand, and the carrier substrate 2, on the other hand, a barrier layer 14 in each case forms a gas-tight surface region 33, 34, 35 and acts as an adhesion promoter between the connections 5, 27 and the porous carrier substrate 2.

The barrier layer 14 covers the top side 4 of the carrier substrate 2 outside the electrode structure 20 and thus closes diffusion openings in the carrier substrate 2 which are formed outside the electrode structure 20.

This prevents gas from being able to emerge from the measurement gas line 16 outside the gas sensor 1.

A cover layer 17 surrounds the electrolyte layer 6 on the outer side and thus protects the gas sensor 1.

Instead of or in addition to the cover layer 17, a housing part 15 (cf. FIG. 1) can be provided on the outer side, which housing part reaches around the gas sensor 1 on the outer side and/or closes it off so as to form a housing.

In further exemplary embodiments, in a modification of FIG. 4, an opening is formed in the region of the gas sensor 1 in the tube wall of the measurement gas line 16, a carrier substrate 2 in the form of a membrane or a film being placed onto said opening or an insert comprised of a porous material being inserted into said opening. The carrier substrate 2 thus closes the recess mentioned. Diffusion openings are formed in the film or membrane and connect the underside 3 to the top side 4 of the film- or membrane-like carrier substrate 2 or of the insert mentioned. Gas-tight surface regions that bear the connections of the electrodes are formed on the membrane, or the connections are applied on gas-tight surface regions adjacent to the membrane.

An electrode structure 20 having connections 5, 27, 28, a catalyst layer 10 forming the measurement electrodes 25, 26, an electrolyte layer 6 and a cover layer 17 is formed at the top side 4 of said carrier substrate 2 in a corresponding arrangement analogously to the exemplary embodiment according to FIG. 4. The diffusion openings not required are sealed with a barrier layer 14.

Figure 5:
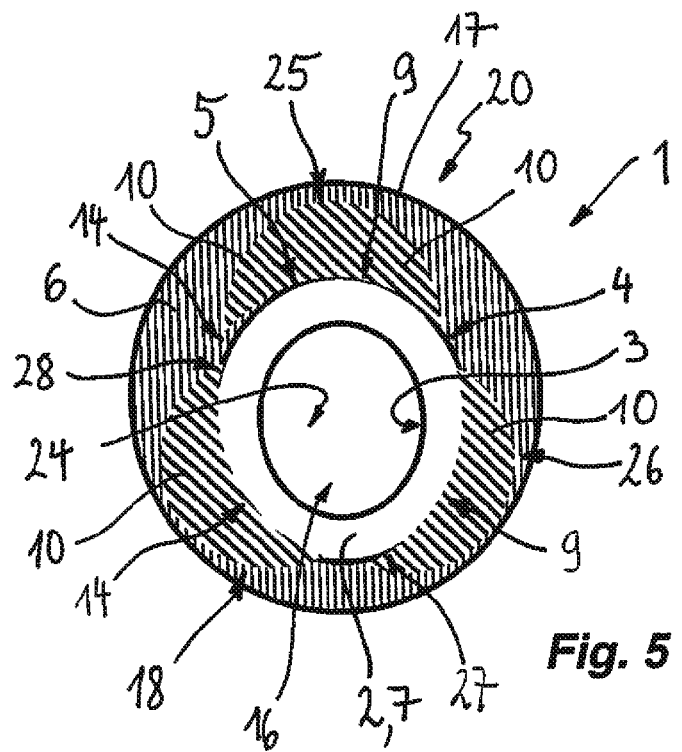
FIG. 5 shows a further gas sensor according to the invention with a tubular carrier substrate in a greatly simplified radial sectional illustration.

In the exemplary embodiment according to the invention in accordance with FIG. 5, the carrier substrate 2 is likewise embodied in a tubular fashion.

FIG. 5 illustrates a greatly simplified, schematic radial section of the gas sensor 1.

On the inner side, the carrier substrate 2 forms an underside 3. On the outer side, the carrier substrate 2 forms a top side 4. The underside 3 forms a gas inlet 24.

Diffusion openings (not illustrated any further) are formed naturally in the integral carrier substrate 2, said diffusion openings connecting the underside 3 to the top side 4.

Through said diffusion openings, measurement gas can diffuse from the measurement gas line 16, formed by the tubular carrier substrate 2, into the catalyst 10 and the electrolyte layer 6. In this case, the catalyst layer 10 for forming the measurement electrodes 25, 26 and the reference electrode 18 at the top side 4 is applied to the connections 5, 27, 28. The electrolyte layer 6 surrounds the carrier substrate 2 radially on all sides.

The electrode structure 20 has at least three electrodes, of which two electrodes can be used as measurement electrodes 25, 26 and one electrode can be used as reference electrode 18. In the region of said reference electrode 18, the diffusion openings below the electrode structure 20 as well are closed or sealed with a barrier layer 14. The barrier layer 14 also extends below the connections 5, 27, 28, where it forms gas-tight surface regions 33, 34, 35 (cf. FIG. 3) on which the respective connection 5, 27, 28 adheres.

Such a reference electrode 18 is also formed in the above-described exemplary embodiments in a manner known per se.

In the exemplary embodiment in accordance with FIG. 5, the electrolyte layer 6 is closed off on all sides toward the outside by a cured cover layer 17.

The gas sensor 1 thus extends over a section of the measurement gas line 16.

It should also be mentioned that the housing part 15 in FIG. 1 is embodied in a trough-shaped fashion with a recess 30 for accommodating the electrolyte layer 6.

Figure 6:
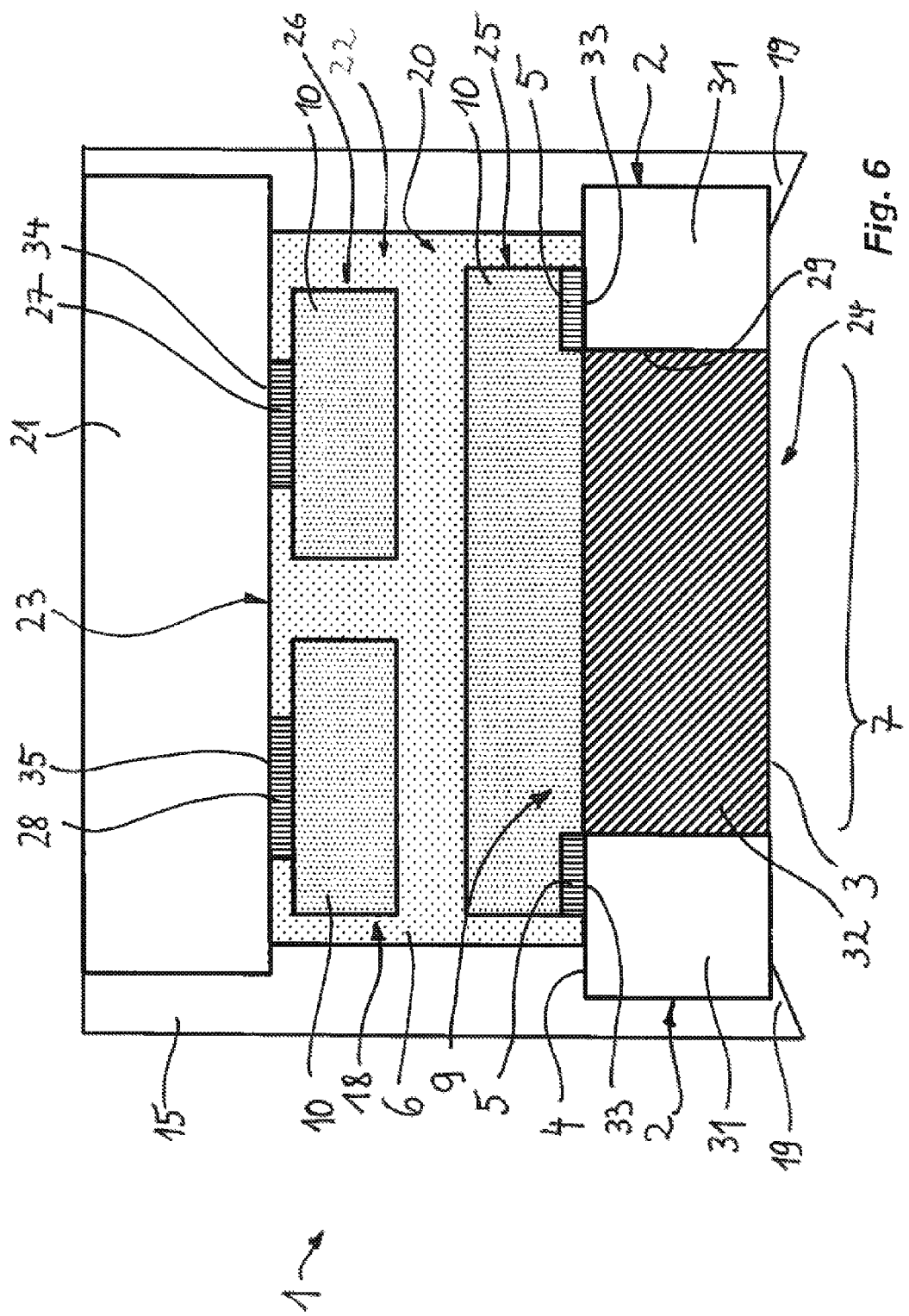
FIG. 6 shows a further gas sensor according to the invention in a sandwich design in a greatly simplified sectional illustration.

FIG. 6 shows a further gas sensor 1 according to the invention. The above explanations with regard to the reference signs are correspondingly applicable. In contrast to the planar constructions described above, the gas sensor 1 in accordance with FIG. 6 is embodied in a sandwich design. This means that a plurality of electrode structures 20, 22 are arranged in a stacked arrangement, that is to say one above another.

For this purpose, the gas sensor 1 has a first carrier substrate 2 and a second carrier substrate 21, which are stacked one above the other.

The electrolyte layer 6 is arranged between the first carrier substrate 2 and the second carrier substrate 21.

The second carrier substrate 21 thus partly forms the housing for the electrolyte layer.

The first carrier substrate 2 is embodied integrally or in a multipartite fashion as described above. Therefore, the explanations above are respectively correspondingly applicable here to the same reference signs.

The second carrier substrate 21 is produced from a gas-tight material or is at least not connected to the gas inlet 24. An electrode structure 22 having a reference electrode 18 and a counterelectrode 26 is formed on the second carrier substrate 21, that is to say at the surface 23 of the electrolyte layer 6 which faces away from the gas inlet 24.

The working electrode 25 is formed at the carrier substrate 2 which is joined to the gas inlet or connected to the gas inlet.

Consequently, the measurement gas can penetrate through the porous regions 7 of the carrier substrate 2 into the measurement electrodes 25.

The measurement gas diffuses further through the electrolyte layer 6 to the counterelectrode 26. In further exemplary embodiments, the counterelectrode 26 can be formed on the carrier substrate 2 and/or can be connected to the or a dedicated gas inlet. For this purpose, the carrier substrate 21 can have a dedicated porous region, for example in a manner shown in FIG. 1 or 2.

The carrier substrate 21 is kept at a distance from the carrier substrate 2 by a housing part 15. The housing part 15 surrounds the electrolyte layer 6 between the carrier substrates 2, 21 on the outer side and—as also in FIGS. 1 and 2—is latched with the carrier substrate 2 by means of latching lugs 19.

The carrier substrates 2, 21 with the measurement electrodes 25, 26 and the reference electrode 18 and also the electrolyte layer 6 are thus accommodated in the recess 30 of the housing part 15 and protected against mechanical, chemical and physical loading from outside.

Instead of the housing part 15, the gas sensor 1 can also be potted with a preferably cured cover layer.

In FIG. 6, the second or upper carrier substrate 21 is produced from a gas-tight material. In the region of the bearing areas of the connections 27, 28 of the electrodes 26, 18, therefore, a gas-tight surface region 34, 35 is respectively formed, to which the connections 27, 28 are applied.

In the exemplary embodiments described, the catalyst layer 10 is applied in dissolved form or as an emulsion and subsequently dried. This gives rise to an electrically conductive structure which forms the measurement electrodes 25, 26 and/or the reference electrode 18 and performs catalytic functions during the detection of the measurement gas. The catalyst layer 10 is thus porous and absorbs electrolyte from the electrolyte layer.

The connections 5, 27, 28 can be produced from gold.

It can be seen that the catalyst layer 10 in each case covers the connections 5, 27, 28, wherein the connections 5, 27, 28 are led out from the covering region with contact-making tracks 36.

In the exemplary embodiments, the catalyst layer 10 of the working electrode 25 is arranged in a manner electrically isolated and spaced apart from the catalyst layer 10 of the counterelectrode 26.

Both measurement electrodes 25, 26 are electrically isolated from the catalyst layer 10 of the reference electrode 18.

In the exemplary embodiments described and in further exemplary embodiments, the electrolyte layer 6 is in each case embodied in gel form by addition of particulate or particle-type constituents to a liquid. This makes it more difficult for the electrolyte layer 6 to emerge through the diffusion openings.

In an electrochemical gas sensor 1, a carrier substrate 2 has an underside 3 and a top side 4, wherein an electrode structure 20 with an electrolyte layer 6 is arranged at the top side 4, while a gas inlet for a measurement gas is formed at the underside 3. It is proposed to form a region 7 comprised of a porous material in the carrier substrate 2, such that diffusion openings in the porous material connect the underside 3 to the top side 4 in a gas-permeable manner, wherein a connection 5, 27 of a measurement electrode 25, 26 is formed in a gas-tight surface region 33, 34, 35 at the top side 4 adjacent to the porous region 7 and the connection 5, 27 is at least partly covered by the electrolyte layer 6.

The invention claimed is:

1. A gas sensor (1) comprising a carrier substrate (2) having a top side (4) and an underside (3), a gas inlet (24) for a measurement gas is formed at the underside (3) and an electrode structure (20) with an electrolyte layer (6) is arranged on the top side (4), the carrier substrate (2) has a porous region (7) comprised of a porous material and the porous material forms diffusion openings that connect the underside (3) to the top side (4), a gas-tight surface region (33, 34, 35) is formed on the carrier substrate (2) at the top side (4) adjacent to the porous region (7), connections (5, 27, 28) of measurement electrodes (25, 26) of the electrode structure (20) are formed as a metallic coating on the gas-tight surface region (33, 34, 35), and the electrolyte layer (6) at least partly covers the connections (5, 27, 28) and the porous region (7), the electrode structure (20) has at least two of the measurement electrodes (25, 26) and a reference electrode (18), and at least one of the measurement electrodes (25, 26) or the reference electrode (27) has a catalyst layer (10) arranged between a respective one of the connections (5, 27, 28) and the electrolyte layer (6).

2. The gas sensor (1) according to claim 1, wherein the connections (5, 27, 28) form through-openings (9) for the measurement gas.

3. The gas sensor according to claim 1, wherein a reference electrode (18) is arranged completely on a gas-tight surface region (35), and the gas-tight surface region (33, 34, 35) is formed by a barrier layer (14).

4. The gas sensor (1) according to claim 1, wherein the diffusion openings are formed by at least one of sintering, use of volatile fillers or expanded plastic, by an etching process, or by filling or equipping a continuous opening (29) in the carrier substrate (2), which is gas-tight, with a porous material.

5. The gas sensor (1) according to claim 1, wherein the carrier substrate (2) is planar.

6. The gas sensor (1) according to claim 1, wherein the carrier substrate (2) is at least one of tubular or part of a measurement gas line (16).

7. The gas sensor (1) according to claim 1, wherein the carrier substrate (2) is produced from a flexible material.

8. The gas sensor (1), wherein the electrolyte layer (6) is continuous and covers the measurement electrodes (25, 26).

9. The gas sensor (1) according to claim 1, wherein at least one of the connections (5, 27, 28), the catalyst layer (10), or the electrolyte layer (6) are applied by coating or the electrolyte layer (6) is in gel form.

10. The gas sensor (1) according to claim 1, wherein the catalyst layer (10) covers the connections (5, 27, 28).

11. The gas sensor (1) according to claim 1, wherein at least one of a cured cover layer (17) or a housing (15) is located on at least an outer side around the electrolyte layer (6).

12. The gas sensor (1) according to claim 1, wherein there are at least two of the carrier substrates (2, 21) that are arranged in a manner spaced apart from one another in a sandwich design, and the electrode structure (5, 22) in each case is at least one of formed on said carrier substrates, or the electrolyte layer (6) is arranged between the two carrier substrates (2, 21).

13. The gas sensor (1) according to claim 1, wherein a reference electrode (18) is formed at a surface (23) of the electrolyte (6) which faces away from the gas inlet (24).

14. The gas sensor (1) according to claim 1, wherein the porous material is hydrophobic, and the electrolyte is water-based.

15. The gas sensor (1) according to claim 1, wherein the catalyst layer (6) at least partly covers the connection (5, 27) and the porous region (7).

16. The gas sensor (1) according to claim 1, wherein each of the connections (5, 27, 28) surround the porous region (7) with a ring-shape.

17. The gas sensor (1) according to claim 3, wherein the barrier layer is comprised of gas-tight PTFE, or as a top side of a gas-tight material formed of gas-tight PTFE or ceramic, of the carrier substrate (2).

18. The gas sensor (1) according to claim 1, wherein the electrolyte layer (6) is embodied in a continuous fashion and covers the measurement electrodes (25, 26) and a reference electrode (18), and the connections (5, 27, 28) of the measurement electrodes (25, 26) and of the reference electrode (18) are embodied as a gold coating.

19. The gas sensor (1) according to claim 1, wherein the electrolyte layer (6) covers at least one of the top side (4) of the carrier substrate (2), the electrode structure (20), or the catalyst layer (10).

* * * * *